US006180605B1

(12) United States Patent
Chen et al.

(10) Patent No.: US 6,180,605 B1
(45) Date of Patent: *Jan. 30, 2001

(54) COMPOSITION WITH ENHANCED OSTEOGENIC POTENTIAL, METHOD FOR MAKING THE SAME AND THERAPEUTIC USES THEREOF

(75) Inventors: Charles C. Chen, Potomac, MD (US); Steven R. Jeffries, York, PA (US)

(73) Assignee: GenSci OrthoBiologics, Inc., Irvine, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 09/002,674

(22) Filed: Jan. 5, 1998

Related U.S. Application Data

(63) Continuation of application No. 08/312,091, filed on Sep. 28, 1994, now Pat. No. 5,707,962.

(51) Int. Cl.⁷ .................................................. A61K 38/00
(52) U.S. Cl. .............................. 514/12; 514/21; 514/801; 424/85.1; 424/422; 424/423; 424/424; 530/351; 530/356; 530/399; 530/840; 128/DIG. 8
(58) Field of Search .............................. 514/12, 21, 801; 424/85.1, 422, 423; 530/351, 356, 399, 840; 128/DIG. 8

(56) References Cited

U.S. PATENT DOCUMENTS

| 4,394,370 | * | 7/1983 | Jefferies | 424/15 |
| 5,073,373 | | 12/1991 | O'Leary et al. | 424/422 |
| 5,236,456 | * | 8/1993 | O'Leary et al. | 623/16 |
| 5,284,655 | | 2/1994 | Bogdansky et al. | 424/422 |
| 5,290,558 | | 3/1994 | O'Leary et al. | 424/422 |
| 5,531,791 | | 7/1996 | Wolfinbarger, Jr. | 623/16 |
| 5,626,861 | | 5/1997 | Laurencin et al. | 424/426 |
| 5,707,962 | * | 1/1998 | Chen et al. | 514/12 |
| 5,766,618 | | 6/1998 | Laurencin et al. | 424/426 |
| 5,866,155 | | 2/1999 | Laurencin et al. | 424/425 |

FOREIGN PATENT DOCUMENTS

WO 89/04646 * 6/1989 (WO).

* cited by examiner

Primary Examiner—Christopher S. F. Low
Assistant Examiner—Abdel A. Mohamed
(74) Attorney, Agent, or Firm—Howrey Simon Arnold & White

(57) ABSTRACT

The present invention provides improved osteogenic compositions having enhanced by the sorption of growth factors, of nutrient factors, or drugs onto or into the compositions. Compositions may consist of collagen and demineralized bone materials onto and into which growth factors, antimicrobial agent,s nutrient factors, or other soluble factors may be sorbed to enhance the osteogenic factor. These materials can be used in a wide range of clinical procedures to replace and restore osseous or periodontal defects.

8 Claims, No Drawings

COMPOSITION WITH ENHANCED OSTEOGENIC POTENTIAL, METHOD FOR MAKING THE SAME AND THERAPEUTIC USES THEREOF

This is a continuation of U.S. patent application Ser. No. 08/312,091, filed Sep. 28, 1994, now U.S. Pat. No. 5,707,962.

FIELD OF THE INVENTION

This invention is in the field of osteogenic bone repair compositions. More specifically this invention relates to bone repair compositions having enhanced osteogenic potential, to methods for making these bone repair compositions having enhanced osteogenic potential and to therapeutic uses for these compositions.

BACKGROUND OF THE INVENTION

A variety of methods and compositions of biomaterials have been used to repair or regenerate bone loss due to either trauma or disease. Conventional implantable bone repair materials provided a matrix or scaffolding for migration into, proliferation and subsequent differentiation of cells responsible for osteogenesis (Nashef U.S. Pat. No. 4,678,470). While the compositions provided by this approach provided a stable structure for invasive bone growth they did not promote bone cell proliferation or bone regeneration. Subsequent approaches have used bone repair matrices containing bioactive proteins which when implanted into the bone defect provided not only a scaffolding for invasive bone ingrowth, but active induction of bone cell replication and differentiation. In general these osteoinductive compositions are comprised of a matrix which provides the scaffolding for invasive growth of the bone, and anchorage dependent cells and an osteoinductive protein source. The matrix may be a variety of materials, such as collagen (Jefferies U.S. Pat. Nos. 4,394,370 and 4,472,840) or inorganically based, such as a biodegradable porous ceramic (Urist U.S. Pat. No. 4,596,574) or polylactic acid (Urist U.S. Pat. No. 4,563,489). In particular, two specific substances have been well established in their ability to induce the formation of new bone through the process of osteogenesis: demineralized bone particles or powder, and bone morphogenetic proteins (BMPs) (Urist U.S. Pat. Nos. 4,595,574, 4,563,489, 4,551,256). A variety of other bone inducing factors have been characterized as well (Seydin et al., U.S. Pat. No. 4,627,982).

Osteogenic compositions and method for making the same are described in Jefferies U.S. Pat. Nos. 4,394,370 and 4,472,840. Jefferies describes complexes of reconstituted collagen and demineralized bone particles or complexes of reconstituted collagen and a solubilized bone morphogenetic protein, fabricated into a sponge suitable for in vivo implantation into osseus defects. Structural durability of these compositions is enhanced by crosslinking with glutaraldehyde. While a wide variety of osteoinductive compositions have been used in bone repair and regeneration there is always need in the art for improvements or enhancements of existing technologies which would accelerate and enhance bone repair and regeneration allowing for a faster recovery for the patient receiving the osteogenic implants.

SUMMARY OF THE INVENTION

This invention relates to bone repair compositions having enhanced osteogenic potential. The osteogenic-bone repair composition of this invention are used as implants to repair, form, or regenerate bone in the treatment of osseous or periodontal defects. These improved osteogenic compositions provided herein comprise a porous or semi-porous matrix and at least one osteogenic factor, wherein one or more growth factors, drugs, nutrients, antimicrobial agents, blood proteins or products, or calcium containing compounds have been sorbed onto or into the matrix of the osteogenic composition complexed with the osteoinductive factor. The osteogenic bone repair material of this invention, produced by the methods described herein, exhibit enhanced osteogenic potential relative to known osteogenic bone repair compositions used as implants to repair bone defects.

It is a general object of this invention to provide improved osteogenic compositions comprising a porous or semi-porous matrix and at least one osteogenic factor, wherein at least one growth factor has been sorbed into or onto the matrix.

It is a more specific object of this invention to provide a improved osteogenic composition comprising a porous or semi-porous collagen matrix and either demineralized bone particles or Bone Morphogenic Proteins, or proteins wherein the growth factor TGF-$\beta$2 has been sorbed onto or into the matrix.

It is a further object of this invention to provide improved osteogenic compositions comprising a porous or semi-porous matrix and at least one osteogenic factor, wherein at least one nutrient factor has been sorbed onto or into the matrix.

It is yet another object of this invention to provide improved osteogenic compositions comprising a porous or semi-porous matrix and at least one osteogenic factor wherein at least one drug has been sorbed onto or into the matrix.

It is yet another object of this invention to provide improved osteogenic compositions comprising a porous or semi-porous matrix and at least one osteogenic factor wherein a at least one antimicrobial, blood protein or product, or calcium containing compound has been sorbed onto or into the matrix.

It is a further object of this invention to provide methods of making the improved osteogenic compositions.

It is yet a further object of this to provide methods of use for these improved osteogenic compositions in the repair of osseous or periodontal defects.

Further objects and advantages of the present invention as will become apparent from the description that follows.

DETAILED DESCRIPTION OF THE INVENTION

The present invention relates to osteogenic compositions having enhanced osteogenic potential. The compositions having enhanced osteogenic potential provided herein are based on an observation by the inventor that specific combinations of osteoinductive factors and growth factors have a synergistic effect in enhancing bone repair. This present invention further relates to osteogenic composition having enhanced osteogenic potential comprising combinations of osteoinductive factors and, nutrient factors, drugs, antimicrobial agents, calcium containg compounds, blood proteins or products or other agents which result in enhanced hard tissue healing or bone repair.

The osteogenic compositions provided herein and having enhanced osteogenic potential are comprised of a porous or semi-porous matrix and at least one osteoinductive factor, wherein at least one growth factor has been sorbed into or onto the matrix. Composition comprising a porous or semi-porous matrix and a osteoinductive element are comprised of materials known in the art and prepared by known methods. The matrix may be comprised of organic, materials, inorganic materials, such as ceramics, or synthetic polymers. Examples of organic materials that can be used to form the matrix include, but are not limited to, collagen, polyamino acids, or gelatin. The collagen source maybe allogenic, or xenogeneic relative to the mammal receiving the implants. The collagen may also be in the form atelopeptide or telopeptide collagen. Example of synthetic polymers that can be used to form the matrix include, but are not limited to, polylactic acids, polyglycolic acids, or combinations of polylactic/polyglycolic acids. Resorbable polymers, as well as non-resorbable polymers such as may constitute the matrix material. One of skill in the art will appreciate that the terms porous or semi-porous refers to the varying density of the pores in the matrix. One of skill in the art will also appreciate that inorganic fillers or particles, such as hydroxyapatite, tri-calcium phosphate, ceramic glasses such as Bioglass, amorphous calcium phosphates, porous ceramic particles or powders, mesh or particulate titanium or titanium alloy may also be added to the organic or synthetic matrix. Mineralized or partially mineralized freeze-dried, particulate bone may also be used for this purpose.

Examples of osteogenic factors that may be complexed with the matrix include, but are not limited to demineralized bone particles, Bone Morphogenetic Proteins (BMP), such as BMP-2 and BMP-7, and other osteoinductive factors such as extracts of demineralized bone matrix. Examples of other BMPs which may be complexed with the matrix by conventional methods include, but are not limited to, BMP-2a, BMP-4, BMP-5, BMP-6, BMP-8 (Wozney, J. M. and Rosen V: "The BMP's In Bone Development And Repair," Portland Bone Symposium, Jun. 21–24, 1993). The use of the term demineralized bone particle herein is intended to encompass bone particles of a wide range of sizes and bone powders.

This invention relates to osteogenic compositions comprising a porous or semi-porous matrix and at least one osteogenic factor, wherin one or more growth factors have been sorbed into and onto the matrix complexed with the osteogenic factor. Examples of growth factors that may be used for sorption into and onto the porous or semi-porous matrix that has been complexed with a osteogenic factor or factors include, but are not limited to, Transforming Growth Factor-Beta (TGFβ), such as TGFβ1, TGFβ2, and TGFβ3, Transforming Growth Factor-Alpha (TGF-x), Epidermal Growth Factor (EGF), Insulin Like Growth Factor-I and II, Interleukin-I (IL-I), Interferon, Tumor Necrosis Factor, Fibroblast Growth Factor (FGF), Platelet Derived Growth Factor (PDGF), Insulin-like Growth Factor (KGF-1), and Nerve Growth Factor (NGF). Cytokines and prostoglandins may also be sorbed into or onto the porous or semi-porous matrix which has been complexed with an osteogenic factor or factors. The growth factors used in the compositions of the invention may be of natural origin or recombinently produced by conventional methods. Such growth factors are also commercially available. Combinations of two or more growth factors may be applied to the osteogenic compositions to further enhance osteogenic or biologic activity of the implants.

By way of example, the osteogenic composition may comprise collagen as the porous or semi-porous matrix and demineralized bone particles as the osteoinductive factor. A preferred method for producing the reconstituted collagen to be used in the collagen/demineralized osteogenic bone compositions is by dispersing natural insoluble collagen in an acid or alkaline solution, homogenizing the dispersion in a Waring Blender under cold [4° Centigrade (C.)] conditions. One of skill on the art will understand that the collagen dispersion may be treated with the enzyme Ficin to remove non-collagen proteins and cellular material, and/or may be treated with other proteolytic enzymes, such as pepsin or trypsin, to remove telopeptide regions of the collagen macromolecule, thus reducing antigenicity if a non-allogenic natural tissue source is used to extract the collagen. Hypertonic salt may be added to the collagen dispersion to effect precipitation of the solubilized collagen, or the acid dispersion is dialyzed against saline at physiologic pH 7.4 to promote fibrilogenesis. The precipitate can be spun down in a medium to high speed ultra-centrifuge and resuspended in a dilute acid or base solution to effect resolubilization. By way of example, the optimal pH ranges for the solubilized or dispersed collagen suspensions are anywhere from about pH 1.5 to 5.5 in the acid range and from about pH 8.0 to 12.0 in the alkaline range. The source of the collagen may be from human or animal sources, or could be in a recombinant form expressed from a cell line, or bacteria. Human sources are preferred. Once the collagen has been extracted from the tissue, the purified collagen may either be in the form of an aqueous acidic or basic dispersion, or alternatively, as a lyophilized dry powder or fleece as an acidic or basic collagen salt. The use of one or more purified or partially purified Bone Morphogenetic Proteins, preferably BMP-2 OR BMP-7, or combinations thereof may be substituted for the use of particulate demineralized bone powder( Jefferies U.S. Pat. Nos. 4,394,370 and 4,472,840). A weight of BMP ranging from the micrograms to milligrams of BMP to milligrams of collagen may be used. By way of example, 100 micrograms of BMP per milligram collagen may be used.

Demineralized bone particle or powder or Bone Morphogenetic Protein or proteins, such as BMP-2, BMP-2a, or BMP-7, may then be blended with the collagen matrix by conventional methods, such as a powder blend, as a hydrated or liquid form added to the dry collagen powder or fleece, as a dry lyophilized powder into an aqueous collagen dispersion, or as a hydrated or liquid form of the demineralized bone powder or of the Bone Morphogenetic Protein or Proteins. Specific methods of combining reconstituted collagen with demineralized bone particles or and/or bone morphogenetic protein are described by Jefferies in U.S. Pat. Nos. 4,394,370 and 4,472,840 which are herein incorporated by reference.

The collagen/demineralized bone osteogenic composition described above can be produced in the form of a dehydrated form of a sponge, powder, particles, membrane, fleece or fibers by standard methods known to one of skill in the art. The collagen/demineralized bone sponge may be ground into a particles, powder or fleece by conventional methods. The weight ratio of the collagen to demineralized bone particles may be similar to that described in Jefferies et al., U.S. Pat. No. 4,394,370. Alternatively, the weight ratio may range from 10% to 60% collagen and 40% to 90% demineralized bone particles.

In one embodiment, this invention provides improved osteogenic composition for use as implants comprising a matrix of collagen complexed with demineralized bone particles, BMP, BMPs or combinations thereof to which is added, by sorption onto or into the porous or semi-porous matrix structure, an aqueous solution containing one or more soluble growth factors. The collagen matrix complexed with the osteogenic factor to which the soluble growth factor is to be sorbed, may also be in the form of a semi-porous or porous sponge, (Jefferies U.S. Pat. Nos. 4,394,370 and 4,472,840) a membrane, a fiber-like structure, powder, fleece, particles or fibers. The growth factor or factors may be delivered to the collagen demineralized bone compositions in a liquid form, but can be provided in a dry state prior to reconstitution and administrated by sorption onto or into the collagen-demineralized bone or BMP compositions. One of skill in the art will appreciate that the growth factor is sorbed onto or into the matrix and may also reside within the void volume of the porous or semi porous matrix.

By way of example, the growth factor TGF-β can be sorbed into or onto the collagen matrix of the collagen demineralized bone osteogenic composition in the form of a sponge. Preferably, the growth factor TGF-β2 is used. The TGF-β2 may be natural or synthetic in origin. The TGF-β2 is contacted with the sponge allowing the growth factor to be sorbed onto or into the matrix and void volume of the porous or semi-porous structure of the sponge. The amount of the TGF-β2 sorbed onto the sponge can range from nanogram to milligram quantities. Preferred amount of TGF-β2 to be sorbed are about 0.1 ng to 500 mg per 40 to 80 mg of sponge, most preferred is about 10 ng to 100 mg and most preferable is about 100 ng to 5 mg. By way of example, a collagen-demineralized bone osteogenic sponge comprising 75 collagen and 25% demineralized bone powder (weight ratio) may have sorbed onto or into the matrix about 5 ug of TGF-β2 per 40 mg of sponge or per 80 mg of sponge.

Yet another embodiment of this invention relates to osteogenic compositions having enhanced osteogenic potential comprising a porous or semi-porous matrix and at least one osteoinductive factor, wherein a nutrient factor, drug or antiinflammatory has been sorbed into or onto the matrix of the osteogenic composition. Examples of nutrient factors that can be used by the methods described herein include, but is not limited to, vitamins, hormones, individual or combination of amino acids, specific inorganic salts and trace elements. Examples of drugs that can be sorbed onto or into the matrix, include, but is not limited to, tetracycline or antimicrobial agents such as chlorahexadine or zinc citrate. Suggested amounts for the drug, are 0.1:1 wt drug/wt collagen ratios. Examples of antiinflammatory factors include, but is not limited to steroidal and nonsteroidal factors such as flurbiprofen. The drugs or calcium containing compounds may be sored onto or into the semiporous or porous matrix as described for the growth factors.

In yet another embodiment blood products such as fibrin, fibronectin, or blood clotting factors may be sorbed onto the matrix. Calcium containing compounds such as calcium hydroxide, calcium lactate and inorganic or organic calcium salts may aiso be sorbed onto the matrix. Large molecular weight proteins, such as enzymes, or extracellular matrix proteins, such as lamin or fibronectin, may also be sorbed to the matrix as described above.

This invention also relates to osteogenic composition having enhanced osteogenic potential comprising a porous or semi-porous matrix and at least one a more osteoinductive factor, wherein a growth factor, nutrient factor, drug calcium containing compound, antimicrobial agent, blood protein or products or combination thereof has been sorbed onto the matrix. In addition, to polypeptide growth factors, glycoproteins, carbohydrates, cell culture medias, and additional Bone Morphogenetic Factor (or Factors) may be sorbed into or onto the matrix of the osteogenic composition structure via sorption of the liquid faction containing the ancillary growth factor(s) or compound(s) as described above.

It will be understood by one of skill in the art that other suitable materials, such as biocompatible polymers, can be substituted for collagen as a matrix material. The growth factors or other agents may be sorbed into or onto the matrix or reside in the matrix void wherein as described above for sorption of the growth factor or factors.

This invention also relates to a method of making an osteogenic implant having enhanced osteogenic potential comprising obtaining a osteogenic composition comprising a porous or semiporous matrix and at least oneosteoinductive factor; and sorbing at least one agent selected from the group consisting of growth factors, nutrient factors, drugs, antimicrobial agents, calcium containing compounds, blood proteins or products or antiinflammatory agents into or onto said porous or semi-porous matrix complexed with said osteoinductive factor.

The porous or semi-porous osteogenic composition, may be chemically crosslinked with agents known in the art (e.g. glutaraldehyde) and dehydrated prior to rehydration with the active factor solution. These materials can be. used therapeutically as a grafting implant in plastic and reconstructive surgery, periodontal bone grafting, and in endodontic procedures and implanted by standard surgical procedures. The osteogenic implants of this invention having enhanced osteogenic potential are suitable for both human and veterinary use.

All books, articles, or patents referenced herein are incorporated by reference. The following examples are by way of illustrative aspects of the invention but are in no way intended to limit the scope thereof.

EXAMPLE 1

The formation of a collagen-demineralized bone conjugate involves the fabrication of osteogenic sponges derived from human or animal, such as bovine, tendon collagen and human, freeze-dried, demineralized bone particles. Human tendon obtained from cadavers at an organ bank was cut into thin slices, preferably 1 to 3 mm in thickness. These tendon slices are washed in 1 M NaCl or some other suitable hypertonic salt solution. Optionally one way substitute a solution of NaOH in a concentration range of from 0.001 to 2 molar (normal), with or without NaCl to assist in the removal of debris and contaminating substances. The tendon slices were removed from the initial washing/decontamination solution and replaced in a washing solution of sterile water with frequent contacts to remove the initial washing solution. The tendon slices are washed with numerous contacts of fresh sterile water anywhere from two to ten times. The tendon slices were then transferred to a metal basket with a perforated bottom and immersed in a one (1) liter beaker filed with approximately 540 ml of phosphate buffer and 540 mg of Ficin (Sigma Chemical Co., St. Louis, Mo.) The ficin activity ranges from about 0.25 go 0.75 units per milligram Ficin. A unit is defined as the amount of Ficin which will produce a Delta A280 of 0.1 per minute at pH 7.0 at 37° C. when measuring TCA soluble products from Casein in a final volume of 1.0 ml (1 centimeter (cm) light path). The tendon slices were subjected to mild agitation in the phosphate buffer-Ficin bath or 30 to 60 minutes at room temperature (20° to 28° C.). Preferably, the tendon slices are washed with several changes of distilled water prior to addition of the dilute (0.01 N) HCl. The tendon slices were immersed in the 0.01 N HCl solution for at least 24 hours at 4 degrees C. At the end of this contact time, the tendon slices in the 0.01 N HCl are transferred to a sterile Waring Blender. The blender was activated in short 15 to 30 second intervals in order to disperse the tendon material into a slurry dispersion. The dispersion and blender vessel were maintained on ice to keep the temperature as close to 4 degrees C. to dissipate the heat generated by the blender and the blending procedure. The dispersed tendon slurry was then, optionally, passed through a 50 to 1000 micron filter (using vacuum) to remove any tendon particles that are not completely dispersed.

The filtered tendon dispersion is precipitated and concentrated by the addition of 1 M NaCl and collected on a sterile glass rod. The collected tendon collagen fiber precipitate was redispersed in a cold solution of sterile water containing approximately a concentration of the acid HCl of 0.01 N HCl (50 ml of 0.01 N HCl per gram of wet weight precipitated collagen material). The precipitate is covered and refrigerated at 2° to 8° C. for 16 to 24 hours. The precipitated collagen material was dispersed in a sterile Waring Blender using short bursts at low speed. The dispersed tendon collagen is then dialyzed against multiple changes (2 to 10 times) of sterile distilled water (3× to 10×volume). The dialyzed tendon collagen dispersion is then freeze-dried (lyophilized) by first freezing the dispersion in labeled trays in a freeze-drier. The collagen was held for 16 to 24 hours at −40 degrees C., the temperature is then raised to −8 degrees C. and the vacuum is initiated. Vacuum is applied for a sufficient time period (approximately 24 to 72 hours) to lyophilize the tendon collagen dispersion. Those skilled in the art will recognize that the wide range of cooling and vacuum cycles may be appropriate to arrive at a satisfactory lyophilized end-product. The resultant sponge-lie material is then shredded into a powder using a Waring Blender. The powdered lyophilized sponge material is stored under sterile conditions until needed for blending into composite osteogenic compositions.

The lyophilized tendon collagen fleece or powder is weighed for dry weight. The tendon powder is proportioned with a portion of dry demineralized bone particles and blended evenly until a uniform dry powder blend is achieved. The weight ratio of collagen to demineralized bone particles may be similar to that described in Jefferies U.S. Pat. No. 4,394,370. Alternatively, the weight ratio of the tendon collagen powder or fleece to demineralized bone powder can range anywhere form about 60% tendon collagen with 40% demineralized bone powder or particles, to about 10% collagen with 90% demineralized bone particles. The powder blends are stored under sterile conditions until needed for reconstitution and lyophilization into an osteogenic sponge form.

In this specific example, pulverized tendon collagen powder or fleece was blended with demineralized bone particles at a weight ratio of 0.66 grams of demineralized bone powder for each gram of dry tendon collagen. For each gram of collagen material in the blended mixture. 50 mls of a solution of sterile water with 4.7% ethanolis is added to the powder blend and mixed to form a thick aqueous dispersion. The mixture was then blended in a Waring Blender with short burst of 5 to 10 seconds on slow speed until the uniformly dispersed ion a aqueous slurry. The collagen bone powder mixture was then poured into anodized aluminum trays and placed in a lyophilizer. The composite sponge was lyophilized in an automated cycle over a 50 hour period, with the lower unit temperature below −40° C. and the upper chamber between 2° and 8° C. The composite tendon collagen-demineralized bone dispersion is first frozen for 10 hours at minus 40° C., then the automatic cycle is initiated to begin the lyophilization. When the lyophilization complete, the intact sponge is removed, cut into desired size sponge pieces, placed in an appropriate package configuration, and then sterilized by E-Beam or Gamma radiation methods. Alternatively, the intact sponge may be pulverized into a fleece powder, or particles using a Waring Blender and dry blending, or using an appropriate dry powder mill.

If a membrane is desired, the composite tendon collagen-demineralized bone dispersion was not lyophilized, but rather poured into an appropriately sized sterile tray or dish, placed in a sterile area or laminar flow box, and allowed to dehydrate into a casted collagen membrane. The membrane can be crosslinked by elevated thermal storage, by UV radiation, or by chemical means such as immersion in a glutaraldehyde solution at concentrations from about 0.005% to 1.0%.

EXAMPLE 2

A collagen composite sponge was prepared as described in Example 1, but a bovine collagen material was used as the collagen fleece or powder. The weight ratio of collagen to demineralized bone powder was about 75% collagen to 25% demineralized bone. Alternatively, the bovine collagen source used may be to hide instead of tendon and prepared by conventional methods.

EXAMPLE 3

An osteogenic collagen sponge was fabricated as described in Example 1, but a lyophilized Bone Morphogenetic Protein was blended with the pulverized tendon collagen particles instead of demineralized bone. A weight of BMP ranging from the micrograms to milligrams of BMP to mg collagen may be used. In this specific example, 100 micrograms BMP extracted from bone by conventional methods (Jefferies U.S. Pat. Nos. 4,394,370 and 4,472,840) and Urist U.S. Pat. No. 4,455,256) per milligram collagen was blended then dispersed in aqueous solution, prior to lyophilization a sponge configuration as described in Example 1. Alternatively, this collagen-BMP composite may be cast into a membrane as described in Example 1, or the sponge configuration may be ground into a powder or fleece.

EXAMPLE 4

A growth factor, in aqueous or liquid form, can be sorbed in and onto the porous structure of a composite osteogenic sponge in the following manner. A collagen-demineralized bone particle sponge was removed from its sterile package and placed in a sterile plastic disposable dish. Approximately 5 micrograms (ug) of Transforming Growth Factor Beta-2 (Celltrex, Palo Alto, Calif.) was reconstituted in sterile saline, and applied with a sterile syringe or pipette to the osteogenic composite sponge. After about 1 to 10 minutes, the sponge with sorbed growth factor was applied to an appropriate osseous defect in normal clinical use. The weight of growth factor applied to a 75–80 mg sponge can range from nanograms to milligram amounts of growth factor in aqueous or liquid form.

EXAMPLE 5

The growth factor or factors are applied to a pulverized sponge powder or fleece as an alternative method. For example, the 5 micrograms of Transforming Growth Factor Beta-2, in sterile saline or physiologic buffer, may be added to the composite powder in a sterile vial, lightly agitated, allowed to stand for 1 to 10 minutes. The hydrated osteogenic powder is then applied to the appropriate osseous defect requiring treatment.

EXAMPLE 6

The growth factor or factors may be applied to a composite osteogenic membrane as described in Example 1. For example, a collagen-demineralized bone membrane consisting of 5 to 10% demineralized bone particles and 90 to 95% collagen material can be rehydrated in a growth factor solution prior to implantation on or into an osseous defect. Alternatively, the membrane may be used as a barrier membrane in a guided tissue regeneration procedure over a periodontal or alveolar defect.

While the invention has been described with reference to certain specific embodiments, it will be appreciated that many more defections and changes may be made by those skilled in the art without departing from the spirit of the invention. It is intended therefore by the appended claims to cover all such modifications and changes as fall within the scope of the invention.

What is claimed is:

1. An osteogenic composition having enhanced osteogenic potential, the composition comprising
   a porous or semi-porous matrix of human or bovine collagen;
   at least one osteoinductive factor; and
   wherein at least one growth factor, nutrient factor, drug, calcium-containing compound, anti-inflammatory agent, blood product, large molecular weight protein, or combination thereof is sorbed into or onto the porous or semi-porous matrix.

2. An osteogenic composition having enhanced osteogenic potential, the composition comprising
   a porous or semi-porous matrix;
   at least one osteoinductive factor; and
   wherein at least one growth factor is sorbed onto or into the porous or semi-porous matrix.

3. The composition of claim 2 wherein the porous or semi-porous matrix, and the at least one osteoinductive factor are provided by a single component of the composition.

4. The composition of claim 2 wherein the at least one osteoinductive factor, and, the at least one growth factor are provided by a single component of the composition.

5. An osteogenic composition having enhanced osteogenic potential, the composition comprising
   a porous or semi-porous matrix;
   at least one osteoinductive factor; and,
   wherein at least one nutrient factor, drug or anti-inflammatory agent is sorbed into or onto the porous or semi-porous matrix.

6. The composition of claim 5 wherein the porous or semi-porous matrix, and the at least one osteoinductive factor are provided by a single component of the composition.

7. The composition of claim 5 wherein the at least one osteoinductive factor, and, the at least one nutrient factor, drug or anti-inflammatory agent are provided by a single component of the composition.

8. The composition of claim 5 wherein at least one nutrient factor is sorbed into or onto the matrix, and wherein the at least one osteoinductive factor, and, the at least one nutrient factor are provided by a single component of the composition.

* * * * *